US011318074B2

(12) United States Patent
Hwang et al.

(10) Patent No.: US 11,318,074 B2
(45) Date of Patent: May 3, 2022

(54) OIL-IN-WATER FORM COSMETIC COMPOSITION

(71) Applicant: AMOREPACIFIC CORPORATION, Seoul (KR)

(72) Inventors: Joon Young Hwang, Yongin-si (KR); Byung Ryol Paik, Yongin-si (KR); Jin Young Yoon, Yongin-si (KR); Soon Ae An, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 484 days.

(21) Appl. No.: 16/471,626

(22) PCT Filed: Sep. 20, 2017

(86) PCT No.: PCT/KR2017/010287
§ 371 (c)(1),
(2) Date: Aug. 14, 2019

(87) PCT Pub. No.: WO2018/056684
PCT Pub. Date: Mar. 29, 2018

(65) Prior Publication Data
US 2019/0365613 A1    Dec. 5, 2019

(30) Foreign Application Priority Data

Sep. 21, 2016    (KR) .................... 10-2016-0120826

(51) Int. Cl.
*A61K 8/06*    (2006.01)
*A61K 8/34*    (2006.01)
(Continued)

(52) U.S. Cl.
CPC .............. *A61K 8/062* (2013.01); *A61K 8/345* (2013.01); *A61K 8/60* (2013.01); *A61Q 19/007* (2013.01)

(58) Field of Classification Search
CPC ........ A61Q 19/00; A61Q 17/04; A61Q 19/10; A61Q 19/08; A61Q 15/00; A61Q 19/02; A61Q 5/02; A61Q 5/12; A61Q 17/02; A61Q 19/007; A61Q 11/00; A61Q 5/00; A61Q 19/04; A61Q 1/02; A61Q 1/04; A61Q 1/06; A61Q 5/006; A61Q 5/06; A61Q 7/00; A61Q 13/00; A61Q 19/004; A61Q 19/008; A61Q 1/00; A61Q 1/10; A61Q 1/12; A61Q 5/002; A61Q 19/001; A61Q 19/06; A61K 2300/00; A61K 8/062; A61K 8/345; A61K 8/922; A61K 8/9789; A61K 36/185; A61K 36/23; A61K 36/238; A61K 36/28; A61K 36/481; A61K 36/489; A61K 36/73; A61K 36/756; A61K 36/78; A61K 36/882; A61K 36/8884; A61K 36/899; A61K 8/042; A61K 8/60; A61K 8/375; A61K 8/39; A61K 2800/48; A61K 8/06; A61K 8/8152; A61K 8/86; A61K 9/0014; A61K 2800/262; A61K 8/25; A61K 8/361; A61K 8/604; A61K 8/73; A61K 2800/51; A61K 2800/75; A61K 47/14; A61K 8/37; A61K 8/416; A61K 8/4913; A61K 8/671; A61K 9/06; A61K 2800/522; A61K 2800/88; A61K 8/02; A61K 8/046; A61K 8/40; A61K 8/42; A61K 8/44; A61K 8/602; A61K 8/63; A61K 8/8158; A61K 8/9794; A61K 2800/21; A61K 2800/30; A61K 47/10; A61K 47/44; A61K 8/0208; A61K 8/585; A61K 8/732; A61K 8/891; A61K 2800/31; A61K 2800/412; A61K 2800/5424; A61K 2800/592; A61K 2800/5922; A61K 2800/92; A61K 31/37; A61K 31/704; A61K 8/0229; A61K 8/31; A61K 8/34; A61K 8/362; A61K 8/447; A61K 8/4926; A61K 8/4973; A61K 8/498; A61K 8/608; A61K 8/65; A61K 8/675; A61K 8/736; A61K 8/8147; A61K 8/88; A61K 8/92; A61K 8/925; A61K 8/97; A61K 9/107; A61K 2800/413; A61K 2800/782; A61K 2800/82; A61K 2800/84; A61K 8/022; A61K 8/0295; A61K 8/04;

(Continued)

(56) References Cited

U.S. PATENT DOCUMENTS

| 2004/0071651 A1 | 4/2004 | Deckner et al. |
| 2010/0189673 A1* | 7/2010 | Jackwerth .............. A61K 8/064 424/66 |
| 2018/0071202 A1 | 3/2018 | Paik et al. |

FOREIGN PATENT DOCUMENTS

| EP | 1 468 668 A2 | 10/2004 |
| KR | 10-2005-0062603 A | 6/2005 |

(Continued)

OTHER PUBLICATIONS

KR1020160056843 translation, Baek et al. (Year: 2016).*

(Continued)

*Primary Examiner* — Audrea B Coniglio
(74) *Attorney, Agent, or Firm* — Sughrue Mion, PLLC

(57) ABSTRACT

A liquid type oil-in-water form cosmetic composition with high transparency. The oil-in-water form cosmetic composition has a transparent or semi-transparent external appearance and shows low viscosity and light texture while exhibiting excellent moisturizing power and flexibility by comprising oil. Therefore, the oil-in-water form cosmetic composition can be realized as a product in the form of a lotion or essence having an excellent feeling of use and high moisturizing power.

7 Claims, 2 Drawing Sheets

(51) Int. Cl.
*A61K 8/60* (2006.01)
*A61Q 19/00* (2006.01)

(58) Field of Classification Search
CPC ........ A61K 8/044; A61K 8/064; A61K 8/068;
A61K 8/20; A61K 8/26; A61K 8/27;
A61K 8/365; A61K 8/4953; A61K 8/556;
A61K 8/678; A61K 8/737; A61K 8/8129;
A61K 8/892; A61K 8/893; A61K 8/90;
A61K 8/965
See application file for complete search history.

(56) References Cited

FOREIGN PATENT DOCUMENTS

| KR | 10-2008-0085301 A | 9/2008 | | |
|---|---|---|---|---|
| KR | 10-2012-0039863 A | 4/2012 | | |
| KR | 10-2012-0042396 A | 5/2012 | | |
| KR | 10-2013-0011800 A | 1/2013 | | |
| KR | 10-2013-0051705 A | 5/2013 | | |
| KR | 10-1295724 B1 | 8/2013 | | |
| KR | 10-2014-0047443 A | 4/2014 | | |
| KR | 10-1490713 B1 | 2/2015 | | |
| KR | 10-2015-0116655 A | 10/2015 | | |
| KR | 10-1589476 B1 | 1/2016 | | |
| KR | 10-2016-0056843 A | 5/2016 | | |
| KR | 1020160056843 | * | 5/2016 | ............... A61K 8/92 |
| KR | 10-2016-0117111 A | 10/2016 | | |

OTHER PUBLICATIONS

International Search Report of PCT/KR2017/010287 dated Dec. 27, 2017.
Written Opinion of the International Searching Authority of PCT/KR2017/010287 dated Dec. 27, 2017.
International Preliminary Report on Patentability of PCT/KR2017/010287 dated Mar. 26, 2019.

* cited by examiner

[Figure 1]
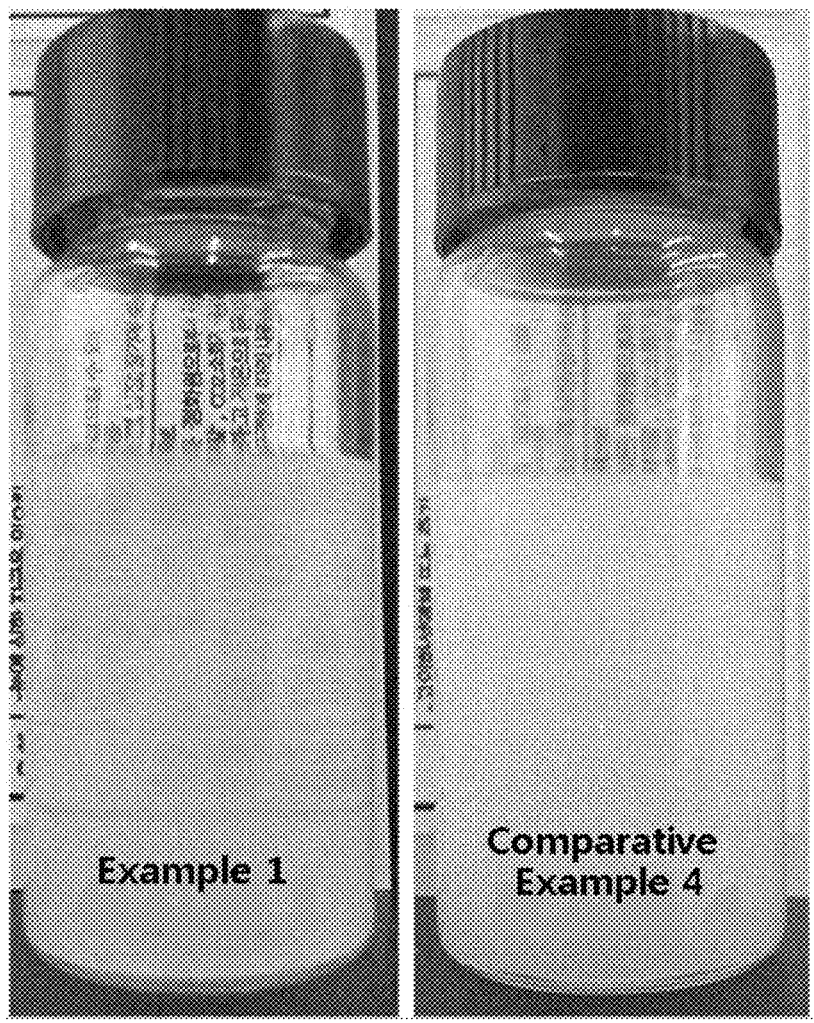

[Figure 2]
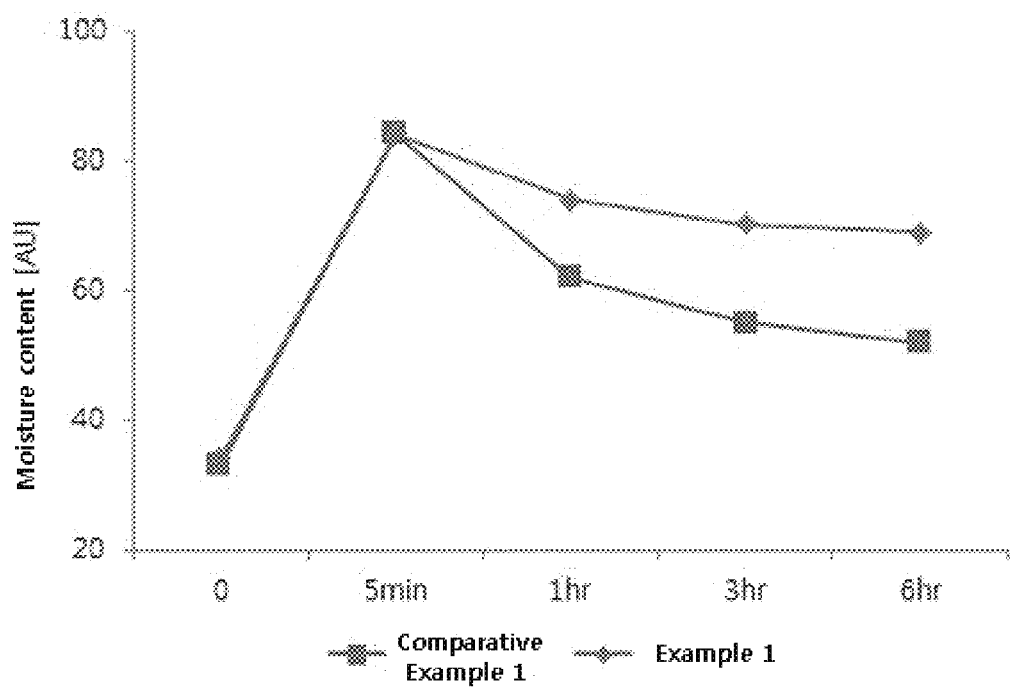

OIL-IN-WATER FORM COSMETIC COMPOSITION

CROSS REFERENCE TO RELATED APPLICATIONS

This application is a National Stage of International Application No. PCT/KR2017/010287 filed Sep. 20, 2017, claiming priority based on Korean Patent Application No. 10-2016-0120826, filed Sep. 21, 2016.

TECHNICAL FIELD

An embodiment is directed to a liquid-type oil-in-water form cosmetic composition having a low viscosity, light texture, and high transparency, while exhibiting excellent moisturizing power and flexibility, by containing at least 3% by weight of oil in the composition.

BACKGROUND ART

In general, emulsified cosmetic products contain an oil phase and a water phase at the same time and thus can realize both advantages of them, so they are widely used as cosmetics.

Meanwhile, in order to satisfy consumers' aesthetic senses by differentiated appearance, studies on cosmetic compositions with a transparent appearance are continuing. As a method for preparing an emulsified cosmetic composition as a transparent formulation, a method of adjusting the refractive indices of the oil phase and water phase to similar values, a method of making a microemulsion by increasing the surfactant content and so on have been reported.

The method of preparing a transparent or semi-transparent emulsion by controlling the refractive indices of the water phase and oil phase is known to produce a transparent formulation only when the difference between the refractive indices of the water phase and oil phase is no more than 0.005. However, since the difference between the refractive indices of water, which is the main component of the water phase, and oil, which is the main component of the oil phase, is large, in order to reduce the difference between the refractive indices of the water phase and the oil phase, an oil having a relatively low refractive index should be selected among the oils, and glycerin, fatty acid, etc. having a relatively high refractive index should be added to the water phase. However, there is a problem that by these components used in the water phase, it has poor emulsification stability and becomes opaque over time.

In addition, in the case of making the microemulsion while increasing the surfactant content, there is a problem that since a large amount of surfactant may cause skin irritation, it is not suitable as a skin care product.

Therefore, it is necessary to develop an emulsified cosmetic composition having an excellent transparency while containing enough oil to impart moisturizing feeling and flexibility when applied to the skin.

PRIOR ART DOCUMENT

Patent Document (Patent Document 1) Korean Patent No. 1295724, Transparent cosmetic composition.

DISCLOSURE

Technical Problem

The present inventors have made efforts to develop an oil-in-water form cosmetic composition having a dilute viscosity suitable for use in liquid products such as skin lotions, and having a transparent or semi-transparent appearance, even while containing oil to provide sufficient moisturizing power, and thus have completed the present invention.

Therefore, it is an object of the present invention to provide a liquid-type oil-in-water form cosmetic composition comprising oil and having a high transparency and a low viscosity.

Technical Solution

In order to solve the above problems, the present invention provides an oil-in-water form cosmetic composition, wherein the oil phase portions containing a surfactant and oil are dispersed in the water phase portion containing a polyhydric alcohol and water, and the average size of the emulsion particles is 200 nm or less and the viscosity is 1000 cps or less.

Advantageous Effects

The oil-in-water form cosmetic composition according to the present invention has a transparent or semi-transparent appearance, and exhibits low viscosity and light texture, even while exhibiting excellent moisturizing power and flexibility by comprising oil. Accordingly, the oil-in-water form cosmetic composition of the present invention can be realized as a skin lotion or essence type product having excellent feeling of use and high moisturizing power.

DESCRIPTION OF DRAWINGS

FIG. 1 is a photograph comparing appearance of cosmetic compositions of Example 1 and Comparative Example 4.

FIG. 2 is a graph showing the measurement results of the moisturizing power of the cosmetic compositions of Example 1 and Comparative Example 1.

BEST MODE

The present invention provides an oil-in-water form cosmetic composition, wherein the oil phase portions containing surfactants and oils are dispersed in the water phase portion containing polyhydric alcohols and water, and the average size of the emulsion particles is 200 nm or less and the viscosity is 1000 cps or less.

The oil-in-water form cosmetic composition of the present invention is prepared using a high-pressure emulsification method, and thus the emulsions containing oils can be dispersed as nano-sized fine particles in the composition. Accordingly, the oil-in-water form cosmetic composition of the present invention exhibits a transparent or semi-transparent appearance and has a low viscosity and light texture and thus can be realized as a liquid formulation such as skin lotion or essence, even though it contains oil with high moisturizing power in an amount of 3% by weight or more.

Hereinafter, the present invention will be described in detail in order that the present invention can be easily carried out by those skilled in the art. The present invention may, however, be embodied in many different forms and should not be construed as limited to the embodiments set forth herein.

The oil-in-water form cosmetic composition according to the present invention has a viscosity of 1000 cps or less, preferably 100 cps or less, more preferably 50 cps or less. By being made to have such low viscosity, the oil-in-water form cosmetic composition of the present invention can be prepared as a light texture formulation, such as a skin lotion or essence, with a feeling of freshness and lightness when applied to the skin.

The composition of the present invention comprises oil, and thus exhibits a soft touch when applied to the skin and has excellent skin moisturizing ability.

The kind of oil that can be used in the present invention is not particularly limited, and examples thereof may be at least one selected from the group consisting of hydrocarbon-based oils including mineral oil, isohexadecane, isodecane, undecane, squalane, alpha olefin oligomers, hydrogenated polydecene, hydrogenated polyisobutene, squalane, and ceresin; natural oils including meadowfoam seed oil, sunflower seed oil, macadamia seed oil, green tea seed oil, ginger oil, *ginseng* oil, coconut oil, olive oil, and *camellia* oil; ester-based oils including cetyl ethylhexanoate, phytosteryl/octyldodecyllauroyl glutamate, isostearyl isostearate, methyl heptyl isostearate, dicaprylyl carbonate, and isopropyl palmitate; ether-based oils including dicaprylyl ether; and silicone oils including dimethicone, cyclopentasiloxane, cyclohexasiloxane, phenyltrimethicone, trisiloxane, and methyltrimethicone.

At this time, the oil may preferably be a mixture of hydrocarbon-based oils, ester-based oils, natural oils, and silicone oils. Specifically, the oil may be a mixture of squalane as a hydrocarbon-based oil, cetyl ethylhexanoate as an ester-based oil, and dimethicone as a silicone oil in a ratio of 4 to 6:3 to 5:1.

The oil is preferably included in an amount ranging from 3 to 10% by weight of the total weight of the cosmetic composition. If the amount of oil in the composition is less than 3% by weight, the ability to moisturize the skin is deteriorated. If the amount of oil in the composition is more than 10% by weight, the cosmetic composition is difficult to secure a transparent appearance, and the viscosity is undesirably increased.

In the oil-in-water form cosmetic composition according to the present invention, the emulsion particles comprising oil are dispersed in the composition at a particle size of 200 nm or less, preferably 150 nm or less, more preferably 110 nm or less, and the oil-in-water form cosmetic composition thus obtained exhibits a transparent or semi-transparent appearance. These fine particles are excellent in dispersibility, so that even when stored for a long time, the particles do not fuse with each other and maintain the particle size.

The oil-in-water form cosmetic composition according to the present invention comprises a surfactant to form the emulsion particles having the nano-size as described above and to disperse the emulsion particles more stably in the composition. At this time, the surfactant is preferably a plant-derived surfactant, and examples of such plant-derived surfactants may be at least one selected from the group consisting of polyglyceryl-based surfactants, alkyl glucoside-based surfactants, and methyl glucose sesquistearate.

The polyglyceryl-based surfactant has a large hydrophilic portion and can effectively pack the interface membrane, and the alkyl glucoside-based surfactant has a high HLB value of 9 to 19, which can effectively reduce the particle size. In addition, the methyl glucose sesquistearate is a mixture of methyl glucoside, monoester and diester of stearic acid, which can effectively stabilize oil particles.

These surfactants are preferably used as a mixture by mixing different kinds of surfactants with each other, rather than using only one kind of these surfactants. When such a mixture is used, the oil-soluble particles can be made smaller and can be stabilized for a long period of time.

The polyglyceryl-based surfactant used in the present invention may be, but is not limited to, at least one selected from the group consisting of polyglyceryl-3 methylglucose distearate, polyglyceryl-2 stearate, polyglyceryl-10 stearate and the like.

The alkyl glucoside-based surfactant used in the present invention may be, but is not limited to, cetearyl glucoside, decyl glucoside, coco-glucoside, C12-20 alkyl glucoside, C10-16 alkyl glucoside and the like.

Preferably, the composition of the present invention comprises a mixture of one of the polyglyceryl-based surfactants, one of the alkyl glucoside-based surfactants, and methyl glucose sesquistearate as a plant-derived surfactant. Most preferably, a mixture of polyglyceryl-3 methylglucose distearate, cetearyl glucoside, and methyl glucose sesquistearate may be used, and the mixing ratio thereof is not particularly limited, but may be preferably 10 to 15:3 to 7:1, more preferably 11 to 13:4 to 6:1.

In the present invention, the surfactant is preferably contained in an amount of 20 to 60 parts by weight based on 100 parts by weight of the oil phase portion excluding the surfactant. If the content of the surfactant is out of the above range, the stability of the emulsion particles in the composition decreases, and thus the phenomenon of suspension or separation may occur, so that the desired effect cannot be obtained. Therefore, the content of the surfactant is appropriately controlled within the above range.

The oil-in-water form cosmetic composition according to the present invention contains a polyhydric alcohol in order to stably maintain the emulsion particles and maintain the transparency of the composition. The polyhydric alcohol contains two or more hydroxyl groups (—OH groups) in the molecule, and is preferably included in the water phase portion including water in the present invention.

The polyhydric alcohol can be used without limitation as long as it is a material ordinarily used in the art, and examples thereof may include at least one member selected from the group consisting of erythritol, xylitol, sorbitol, glycol, glycerin, 1,2-propanediol, 1,3-propanediol, 1,3-butylene glycol, 1,2-pentanediol, 1,2-hexanediol, 1,2-octanediol, dipropylene glycol, polyethylene glycol, and derivatives thereof. Of these, glycerin, 1,3-butylene glycol, and polyethylene glycol are preferably used.

At this time, the polyhydric alcohol is preferably used in an amount of 3 to 50% by weight, more preferably 10 to 30% by weight, based on the total weight of the composition to ensure the above-mentioned effect.

The cosmetic composition according to the present invention may contain an appropriate amount of auxiliary ingredients such as ethanol, extracts, functional ingredients, coloring agents, flavors, thickeners, preservatives and the like commonly used in the production of oil-in-water type cosmetics.

In addition, additives such as gelling agents, water-soluble polymers (animal-plant-based, microbial-based, synthetic-based), antioxidants, pH adjusting agents, antibacterial agents, refreshing agents, moisturizing agents, anti-inflammatory agents, whitening agents, cell activators, rough skin improving agents, blood circulation accelerators, skin astringents, ultraviolet absorbents and the like may be added in a range that does not impair the effect of the present invention.

It is preferable that the water-soluble components are blended in the water phase portion and the oil-soluble components are blended in the oil phase portion.

The method for preparing the oil-in-water form cosmetic composition according to the present invention is not particularly limited, but it is preferable to prepare the oil-inwater form cosmetic composition by a high-pressure emulsification method so that the oil can be dispersed evenly in nanoscale into the composition.

For example, the oil-in-water form cosmetic composition of the present invention can be prepared by the following process.

First, a water phase portion comprising a polyhydric alcohol and water is prepared. At this time, the preparation of the water phase portion can be carried out in a vacuum emulsification vessel capable of controlling the temperature and stirring, and if necessary, can be carried out with stirring or heating to 50 to 80° C.

Separately, an oil phase portion comprising a surfactant and oil is prepared. The method of preparing the oil phase portion may be accompanied by stirring or heating as necessary in the same manner as the above-mentioned method of preparing the water phase portion.

Next, the oil phase portion is added to the water phase portion to prepare a pre-emulsion. The preparation of the pre-emulsion can be carried out by stirring in a vacuum emulsification vessel using a homo-mixer at a speed of 2000 to 4000 rpm for 3 to 10 minutes to obtain an emulsion having a relatively large particle size.

Finally, the temperature of the pre-emulsion is lowered to 40 to 60° C. and a nano-sized emulsion is prepared by a high-pressure emulsification method.

The high-pressure emulsification method may be performed by a high-pressure emulsifier such as a microfluidizer, and may be implemented by applying a shear at 1000 to 1500 atm.

The oil-in-water form cosmetic composition of the present invention prepared by this method exhibits a transparent or semi-transparent appearance by satisfying the average particle size of the emulsion below 200 nm and exhibits low viscosity characteristics.

The oil-in-water form cosmetic composition of the present invention can be implemented as various formulations, and can be applied to cosmetics for skin care such as toilet water, essence, massage materials, pack materials, hand gel, and body gel, but is not limited thereto.

Hereinafter, in order to facilitate understanding of the present invention, preferred examples will be presented. However, it will be apparent to those skilled in the art that the following examples are only illustrative of the present invention and various changes and modifications can be made within the scope and spirit of the present invention, and that such changes and modifications are intended to be within the scope of the appended claims.

EXAMPLES

Production Example 1: Preparation of Oil-in-Water Form Cosmetic Composition

An oil-in-water form cosmetic composition was prepared according to the composition shown in Table 1 (unit: wt. %). At this time, a mixture of a hydrocarbon-based oil, an ester-based oil, and a silicone-based oil (hydrocarbon-based oil (squalane):ester-based oil (cetyl ethylhexanoate):silicone oil (dimethicone)=5:4:1) was used as an oil (raw material 5), and a mixture of glycerin: 1,3-butylene glycol=1:1 was used as a polyhydric alcohol (raw material 7).

TABLE 1

| Order | Component name | Example 1 | Example 2 | Example 3 | Comparative Example 1 | Comparative Example 2 | Comparative Example 3 | Comparative Example 4 | Comparative Example 5 |
|---|---|---|---|---|---|---|---|---|---|
| 1 | Purified water | To 100 | To 100 | To 100 | To 100 | To 100 | To 100 | To 100 | To 100 |
| 2 | Polyglyceryl-3 methylglucose distearate | 1.20 | 0.66 | 2.00 | 1.20 | 1.20 | 0.30 | 3.0 | 1.20 |
| 3 | Methyl glucose sesquistearate | 0.10 | 0.06 | 0.17 | 0.10 | 0.10 | 0.10 | 0.10 | 0.10 |
| 4 | Cetearyl glucoside | 0.50 | 0.28 | 0.83 | 0.50 | 0.50 | 0.50 | 0.50 | 0.50 |
| 5 | Oil | 5.00 | 5.00 | 5.00 | 0.50 | 15.00 | 5.00 | 5.00 | 5.00 |
| 6 | Preservative | 0.20 | 0.20 | 0.20 | 0.20 | 0.20 | 0.20 | 0.20 | 0.20 |
| 7 | Polyhydric alcohol | 20.00 | 20.00 | 20.00 | 20.00 | 20.00 | 20.00 | 20.00 | 20.00 |
| 8 | Ethanol | 2.00 | 2.00 | 2.00 | 2.00 | 2.00 | 2.00 | 2.00 | 2.00 |
| | Preparation method | High-pressure emulsification | High-pressure emulsification | High-pressure emulsification | High-pressure emulsification | High-pressure emulsification | High-pressure emulsification | High-pressure emulsification | General emulsification |

<Preparation Method>

(1) General Emulsification

The raw materials 1 and 6 to 8 of Table 1 were mixed at 70° C. to prepare a water phase portion, and the raw materials 2 to 5 were mixed in a separate container at 70° C. to prepare an oil phase portion. The oil phase portion was added to the water phase portion and stirred with a homo-mixer to prepare an oil-in-water type emulsion.

(2) High-Pressure Emulsification

The emulsion prepared by the above general emulsification method was de-aerated and then subjected to a pressure of 3 cycles or more at 1,000 bar using M-110EH-30 Microfluidizer® Processor (Microfluidics) to prepare a final cosmetic composition.

Experimental Example 1: Evaluation of Physical Properties

The physical properties such as viscosity, stability, and particle size of the cosmetic compositions prepared in Preparation Example 1 were measured by the following methods, and the results are shown in Table 2 below.

(1) Measurement of Viscosity

The viscosity was measured using a Brookfield Viscometer LVDV-II (Spindle No. 2, 12 rpm, 2 min).

(2) Measurement of Stability

The occurrence of component separation was observed while storing each cosmetic composition in thermostatic baths at 45° C., 4° C., and −10° C. for 4 weeks.

(3) Measurement of Particle Size

The particle size of the emulsion particles dispersed in each cosmetic composition was measured using a Malvern Zen 3600 Zetasizer.

TABLE 2

| Component name | Example 1 | Example 2 | Example 3 | Comparative Example 1 | Comparative Example 2 | Comparative Example 3 | Comparative Example 4 | Comparative Example 5 |
|---|---|---|---|---|---|---|---|---|
| Appearance | Transparent | Transparent | Transparent | Semi-transparent | Suspended | Suspended | Suspended | Suspended |
| Viscosity | <50 cps | <50 cps | <50 cps | <50 cps | | | | |
| Stability | Stable | Stable | Stable | Unstable (separated) | Unstable (separated) | Unstable (separated) | Unstable (Creaming) | Unstable (separated) |
| Particle size of emulsion | 60 nm | 109 nm | 98 nm | 149 nm | >1000 nm | >1000 nm | 423 nm | >1000 nm |

Referring to Table 2, it can be seen that when the content of oil is within 10% of the total weight of the composition and the content of surfactant is included in an amount of 20 to 60 parts by weight based on 100 parts by weight of the oil phase portion (oil) excluding the surfactant, the oil-in-water form cosmetic composition has a transparent appearance. Particularly, in the case of Example 1, the turbidity (Turbidimeter HI98703) was confirmed to be in the range of 120 NTU to 310 NTU.

In addition, it can be seen that when the cosmetic composition is prepared by the high-pressure emulsification method, the particle size of the emulsion is obtained to be 200 nm or less within the ranges of the oil and surfactant contents as described above, and thus the stability of the formulation also appears to be excellent.

Experimental Example 2: Evaluation of Moisturizing Power

In order to evaluate the moisturizing power of the cosmetic composition according to the present invention, the following experiment was carried out using the cosmetic compositions of Example 1 and Comparative Example 1. Each of the above cosmetic compositions was applied to forearms of adult males and the moisture content of the skin before and after application was measured using a Corneometer CM825 WL. The results are shown in FIG. 2.

Referring to FIG. 2, it can be seen that the cosmetic composition of Example 1 retains moisture content of 82% or more as compared with immediately after application even after 6 hours have elapsed. On the other hand, the cosmetic composition of Comparative Example 1, which had low oil content, showed a moisture retention rate of 59%, which was significantly lower than that of Example 1.

From the above results, it can be seen that the cosmetic composition of the present invention achieves excellent moisturizing power while realizing low viscosity and light texture.

Experimental Example 3: Sensory Evaluation

The sensory evaluation of each cosmetic composition prepared in Preparation Example 1 was performed on 10 women aged 25 to 35 years, and the results are shown in Table 3 below.

Referring to table 3, it can be seen that the cosmetic compositions of Examples 1 to 3 were evaluated to be excellent in both flexibility and spreadability.

On the other hand, it can be seen that in the case of Comparative Example 1 in which the content of oil was small, the flexibility was found to be very poor, and in the case of Comparative Examples 2 to 5, the particle size of the oil was large and the spreadability was deteriorated.

From the above Experimental Examples 1 to 3, it can be seen that since the oil-in-water form cosmetic composition according to the present invention is prepared by a high-pressure emulsification method and thus the emulsion particles in the composition exhibit a particle size of 200 nm or less, thereby exhibiting excellent stability in formulation, having transparent appearance and low viscosity, and showing excellent moisturizing power, flexibility, and spreadability.

The oil-in-water form cosmetic composition of the present invention as described above is suitable for use in skin lotion or essence type products.

The invention claimed is:

1. An oil-in-water form cosmetic composition comprising emulsion particles wherein oil phase portions containing a surfactant and oil are dispersed in a water phase portion containing a polyhydric alcohol and water, and the emulsion particles have 200 nm or less of average size and 1000 cps or less of viscosity,
   wherein the surfactant is a mixture of polyglyceryl-3 methylglucose distearate, cetearyl glucoside and methyl glucose sesquistearate in a mixing ratio by weight of 10 to 15:3 to 7:1.

2. The oil-in-water form cosmetic composition according to claim 1, wherein the oil is selected from the group consisting of hydrocarbon-based oils including mineral oil, isohexadecane, isodecane, undecane, squalane, alpha olefin oligomers, hydrogenated polydecene, and hydrogenated polyisobutene, and ceresin; natural oils including meadowfoam seed oil, sunflower seed oil, macadamia seed oil, green tea seed oil, ginger oil, *Ginseng* oil, coconut oil, olive oil, and *Camellia* oil; ester-based oils including cetyl ethylhexanoate, phytosteryl/octyldodecyllauroyl glutamate, isostearyl isostearate, methyl heptyl isostearate, dicaprylyl carbonate, and isopropyl palmitate; ether-based oils including dicaprylyl ether; and silicone oils including dimethicone,

TABLE 3

| Component name | Example 1 | Example 2 | Example 3 | Comp. Example 1 | Comp. Example 2 | Comp. Example 3 | Comp. Example 4 | Comp. Example 5 |
|---|---|---|---|---|---|---|---|---|
| Flexibility | +++ | +++ | +++ | + | ++++ | ++ | ++++ | +++ |
| Spreadability | ++++ | ++++ | +++ | +++ | ++ | + | + | ++ | cyclopentasiloxane, cyclohexasiloxane, phenyltrimethicone, trisiloxane, methyltrimethicone, and a combination thereof.

3. The oil-in-water form cosmetic composition according to claim 1, wherein the oil is contained in an amount of 3 to 10% by weight of total weight of the composition.

4. The oil-in-water form cosmetic composition according to claim 1, wherein the surfactant is contained in an amount of 20 to 60 parts by weight relative to 100 parts by weight of the oil phase portion excluding the surfactant.

5. The oil-in-water form cosmetic composition according to claim 1, wherein the polyhydric alcohol is selected from the group consisting of erythritol, xylitol, sorbitol, glycol, glycerin, 1,2-propanediol, 1,3-propanediol, 1,3-butylene glycol, 1,2-pentanediol, 1,2-hexanediol, 1,2-octanediol, dipropylene glycol, polyethylene glycol, and a combination thereof.

6. The oil-in-water form cosmetic composition according to claim 1, wherein the polyhydric alcohol is contained in an amount of 3 to 50% by weight of total weight of the composition.

7. The oil-in-water form cosmetic composition according to claim 1, wherein the composition is in transparent or semi-transparent liquid form.

* * * * *